United States Patent [19]
Olsen

[11] Patent Number: 4,814,464
[45] Date of Patent: Mar. 21, 1989

[54] PROCESS FOR MAKING N-ALKYLPYRROLIDONES

[75] Inventor: Robert J. Olsen, Lisle, Ill.

[73] Assignee: Amoco Corporation, Chicago, Ill.

[21] Appl. No.: 31,544

[22] Filed: Mar. 30, 1987

[51] Int. Cl.$^4$ ............... C07D 201/08; C07D 207/267; C07D 207/404
[52] U.S. Cl. .................................. 548/552; 548/543; 548/548; 548/554
[58] Field of Search ................ 548/543, 545, 552, 554

[56] References Cited

U.S. PATENT DOCUMENTS 3,198,808  8/1965  Himmele et al. .................... 548/554
3,448,118  6/1969  Chichery et al. .................... 548/554
3,812,148  5/1974  Hollstein et al. .................... 548/554

FOREIGN PATENT DOCUMENTS 1031145   1/1950   France .
A089523   7/1967   France .
976939    12/1964  United Kingdom .

Primary Examiner—David B. Springer
Attorney, Agent, or Firm—Reed F. Riley; William H. Magidson; Ralph C. Medhurst

[57] ABSTRACT

An improved process for making N-alkylpyrrolidones from a maleic derivative or a succinic derivative which involves catalytically reducing the maleic derivative with hydrogen to succinic anhydride, if the maleic derivative is the starting point, converting succinic anhydride to a N-alkylsuccinimide by ammonolysis-alkylation with a $C_1$ and $C_4$ alkanol and ammonia, and catalytically reducing the resulting N-alkylsuccinimide to the N-alkylpyrrolidone.

8 Claims, No Drawings

PROCESS FOR MAKING N-ALKYLPYRROLIDONES

BACKGROUND OF THE INVENTION

This invention relates to an improved process for making N-alkylpyrrolidones from maleic or succinic derivatives and, more particularly, to processes which reduce maleic derivative using hydrogen to a succinic derivative, or begin with succinic derivative, which derivative is ammonolyzed-alkylated using ammonia and an alcohol to form a N-alkylsuccinimide which is then reduced with hydrogen to form the corresponding N-alkylpyrrolidone.

N-alkylpyrrolidones, in particular N-methylpyrrolidone, are liquid at reasonably low temperatures and because of their powerful dissolving properties have been employed in numerous applications as an extraction and purification solvent. N-methylpyrrolidone has been used in such processes as acetylene recovery from natural gas, butadiene recovery, the separation of aromatics from nonaromatics, sulfur removal from refinery gases, and the dehydration of gas streams. It also has found application as a polymer solvent, being used in the manufacture of resins, fibers, industrial finishes, and in household specialties to overcome incompatibility and improve product performance. Possessing no active hydrogen, it is classified as an aprotic solvent and finds use as a reaction medium in polymer syntheses, for example, alkylated acetylene preparation etc.

Commercially, N-methylpyrrolidone is produced by reacting acetylene with formaldehyde in the presence of a copper acetylide catalyst to generate butynediol. The latter is then hydrogenated to butanediol which is catalytically cyclodehydrogenated to yield 4-butyrolactone. In a final step the butyrolactone is reacted with methylamine to form N-methylpyrrolidone. This technology has several disadvantages. Methylamine and acetylene are both expensive starting materials and the latter presents handling problems as does the formaldehyde. In addition, yields in the four-step commercial process are less than desirable.

Now it has been found that an improved route to N-alkylpyrrolidones starting with a maleic or succinic derivative is available which offers a substantial improvement in process economics because of reduced starting material and processing costs. The improved process is based in part upon the ammonolysis-alkylation reaction of succinic derivatives with ammonia and an alcohol to form N-alkylated compounds.

The thermal reaction with primary amines to form N-alkylpyrrolidones is well documented in the patent literature. See, for example, U.S. Pat. No. 2,643,257, Ger. Offen. No. 2,164,350 and Brit. Pat. No. 1,367,629. In addition, the alkylation of amides and imides via an alcohol is also described. See *J Am Chem. Soc* 94 679 (1972) and 87, 5261 (1965). For example, phthalimide alkylation to the N-alkylimide has been accomplished in two steps by first making the potassium salt of phthalimide and subsequently reacting it with an alcohol. The use of a combination of ammonia and hydrogen to convert a diethylmaleate/ethanol solution catalytically to 2-pyrrolidone is described by Japanese authors in *Y. Kogyo Kagaku Zasshi* 73,545 (1970). The catalyst was a nickel or cobalt material. Pyrrolidones have been alkylated catalytically via alcohols to N-alkylpyrrolidones by Japanese workers. See, for example, Japanese Kokai No. 76-16,657. Reduction using hydrogen of succinimide and N-methylsuccinimide to pyrrolidone and the N-methyl derivative has also been extensively reported. See, for example, U.S. Pat. Nos. 3,092,639, 3,745,164 and 3,681,387. Equally, hydrogenation of maleic anhydride and its derivative to pyrrolidone and N-alkylpyrrolidones using ammonia and hydrogen is taught in U.S. Pat. Nos. 3,808,240, 3,198,808 and 3,080,377.

SUMMARY OF THE INVENTION

Described herein is a process to form an N-alkylpyrrolidone wherein said alkyl substituent is selected from the group consisting of methyl, ethyl, propyl, isopropyl and butyl substituents comprising:
  converting a compound selected from the group consisting of succinic anhydride, succinic acid, and a dialkyl succinate, where said alkyl is a $C_1$ to $C_4$ alkyl group, to a N-alkylsuccinimide by contacting under reaction conditions, optionally in the presence of a catalyst, said succinic anhydride with ammonia and the corresponding alcohol selected from the group consisting of methanol, ethanol, propanol, isopropanol and butanol; and
  catalytically reducing said N-alkylsuccinimide with hydrogen to form said N-alkylpyrrolidone.

Also described herein is a process to form an N-alkylpyrrolidone wherein said alkyl substituent is selected from the group consisting of methyl, ethyl, propyl, isopropyl and butyl substituents comprising:
  catalytically reducing a maleic derivative selected from the group consisting of maleic acid and maleic anhydride with hydrogen to form succinic anhydride
  converting said succinic anhydride to a N-alkylsuccinimide by contacting under reaction conditions said succinic anhydride with ammonia and the corresponding alcohol selected from the group consisting of methanol ethanol, propanol, isopropanol and butanol; and
  catalytically reducing said N-alkylsuccinimide with hydrogen to form said N-alkylpyrrolidone.

DETAILED DESCRIPTION OF THE INVENTION

The feedstock for the instant process is maleic acid or anhydride or a succinic derivative such as succinic acid, anhydride, or dialkyl ester. If the process begins with maleic acid or anhydride, the compound, neat or dissolved in a solvent such as an alkanol, is catalytically reduced in a hydrogen atmosphere, either in a batch reactor or in a continuous type of reactor, such as a plug flow reactor. Reduction temperatures and pressures are generally held to between about 80° C. and about 300° C. at pressures of about near ambient pressure to about 500 atms. as can be understood by one skilled in the art. A number of hydrogenation catalysts are useful for this process including palladium on carbon, supported nickel, and supported cobalt materials. Supports are generally metal oxides such as alumina, silica-alumina, and silica. In particular, nickel and palladium catalysts have been found to give conversions to the reduced product of 100 percent and selectivities of over 98 percent. Reaction times depend upon temperature, pressure and catalyst used in the reactor, but in general run between about 0.5 hrs. and about 5 hrs. Beneficially, the reaction mixture is agitated to insure good contact between hydrogen and the substrate as might be expected for this heterogeneously catalysed hydrogenation reaction.

The feed for the ammonolysis-alkylation reaction is a succinic derivative such as the anhydride, acid or diester or the reduction product of maleic anhydride, succinic anhydride. The diester is a dialkyl ester of succinic acid where the alkyl group is a $C_1$ to $C_4$ alkyl group, preferably the methyl, propyl, isopropyl or butyl group. Additionally, ammonia and a $C_1$ to $C_4$ alkanol are also used in the process, the latter not being necessary in the event a diester is used which forms the corresponding $C_1$ to $C_4$ alkanol in situ during the reaction. $C_1$ to $C_4$ alkanols useful in this process include methanol, ethanol, propanol, isopropanol, and butanol. Preferred is the use of methanol, ethanol and propanol and, most preferred, is the use of methanol.

The reaction of the substrate, ammonia and the $C_1$ to $C_4$ alkanol is carried out under a pressure of about ambient pressure to about 600 atms., more preferably, about 50 atms. to about 400 atms. The reaction temperature is suitably between about 80° C. and about 400° C., more preferably, between about 100° C. and about 350° C. Reaction times depend to some extent upon the pressure and the temperature employed but generally are in the range of about 0.5 hrs. to about 8 hrs., more preferably about 1 hr. to about 4 hrs. It has been found that longer reaction times are required for N-butyl compounds than are required for N-ethyl compounds. N-methyl derivatives appear to form most rapidly under equivalent reaction conditions. The reaction is conveniently carried out batchwise with stirring although a continuous process in a tubular or plug flow reactor is possible. The substrate can conveniently be added as a solution in the alcohol or a nonreactive solvent, preferably excess of the alcohol is used. This ammonolysis-alkylation reaction can be carried out thermally or with the addition of a catalyst if required.

In the slower reactions, those where the N-alkyl group is larger, for example, where a $C_2$ to $C_4$ alkanol is used, use of a catalyst is beneficial. For example, a trace of iodine, bromine, an alkyl bromide or iodide, or an alkali metal bromide or iodide can usefully increase the speed of the ammonolysis-alkylation reaction. Transition metal catalysts can also be used.

In general, the reaction of the substrate, ammonia and alkanol can be effected with good conversion and selectivity. For example, N-methylsuccinimide can be formed from succinic anhydride with over 90 percent selectivity and 100 percent conversion.

In general, the reactants, substrate, ammonia, and alkanol, are used in about stoichiometric proportions. Too little ammonia or alkanol results in incomplete conversion, and too much ammonia is wasteful and produces undesirable by-products.

The N-alkyl products are generally easily separated from the reaction mixture because of the high conversions and selectivities. Where product separations are required they are carried out generally by distillation or crystalliztion.

Reduction of the N-alkylsuccinimide is accomplished catalytically with hydrogen, either continuously or batchwise. A variety of types of reactors can be used. The N-alkylsuccinimide is added to the reactor neat or dissolved in excess of the alkanol as a solvent. Catalysts useful for this heterogeneously catalyzed reaction are, generally, nickel supported on a metal oxide and other catalyst types such as copper chromite and cobalt supported on a metal oxide and other similar catalysts. In general, temperature and pressure ranges are those expecte by one skilled in the art for a reaction of this kind. A reduction temperature between about 100° C. and about 500° C., more preferably between about 150° C. and about 300° C., and a reduction pressure of between about 10 atms. and about 600 atms., more preferably, between about 20 atms. and about 400 atms. are used, as can be understood by one skilled in the art. Advantageously, the reaction mixture is agitated by stirring or otherwise mixed in order to improve contact between the reactants. Conversions can be as high as 100 percent with selectivities of 80 to 90 percent. Reaction times of course vary with the reduction temperature, pressure and catalyst used, as may be expected by one skilled in the art, but in general lie between about 1 hr. and about 12 hrs., more preferably, between about 1 hr. and about 6 hrs.

Reduction of the organic substrate together with the ammonolysis-alkylation reaction can be accomplished catalytically by adding hydrogen and a reduction catalyst to the reaction mix. By reduction is meant reduction of a carbonyl group. Catalysts useful for the reduction reaction are, generally, nickel supported on a metal oxide, copper chromite, cobalt supported on a metal oxide, and other similar catalysts. In general, temperature and pressure ranges are those expected for a reaction of this kind and are consistent with those required for ammonolysis-alkylation. A reduction temperature between about 100° C. and about 500° C., more preferably between about 150° C. and about 300° C., and a reduction pressure of between about 10 atms. and about 600 atms., more preferably between about 20 atms. and about 400 atms. can be used, as can be understood by one skilled in the art. Advantageously, the reaction mixture is agitated by stirring, or otherwise mixing, in order to improve contact between the reactants. Reaction times of course vary with the reaction temperature and pressure used, as may be expected by one skilled in the art, but in general lie between about 1 hr. and about 12 hrs., more preferably between about 1 hr. and about 4 hrs.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

All reactions were carried out in a stirred 300 cc SS autoclave. Conversions and selectivities were calculated using chromatographic analysis and are expressed in mole percent.

EXAMPLE 1

A 90 g amount of maleic anhydride (MAN) and 9 g of Harshaw Ni-5124T (65% Ni) catalyst were placed in the autoclave and 250 psi of hydrogen was pressured into the reactor after the temperature had been brought to 140° C. The reactor was stirred at 1500 RPM for 2 hrs. after which the reactor was depressurized and the contents removed, cooled and analyzed. MAN conversion was 99% with a 95% selectivity to succinic anhydride (SAN).

A 67 g amount of SAN, 62 g of methanol, and 2.53 g of ammonia were heated 5 hrs. in the autoclave at 300° C. while stirring at 900 RPM. After cooling the product was removed and the SAN was found to be 100% converted at a selectivity to N-methylsuccinimide (NMS) of 90%.

A 90 g amount of NMS was placed in the autoclave together with 9 g of Harshaw Ni 1404T catalyst, and 1600 psig of hydrogen was pressured into the reactor after the temperature had been brought to 230° C. The reactor was stirred for 2 hrs. after which the reactor was depressurized and the contents removed, cooled and analyzed. Analysis showed a 60% NMS conversion with an 89% selectivity to N-methylpyrrolidone (NMP).

The latter reduction was repeated a second time using 9 g of Harshaw Ni-5125T catalyst and a reduction time of 10 hrs. Conversion improved to 86% but the selectivity of 85% found was slightly lower than with the other catalyst.

EXAMPLE 2

A 49.2 g portion of MAN and 12.5 g of palladium on carbon was sealed in the autoclave which was then purged with argon. A 42.3 g amount of ammonium hydroxide and 24 g of methanol were added and 700 psig hydrogen was pressured in. The reactor was heated to 145° C. and held for 1.5 hrs. and then the temperature raised to 270° C. for 10.5 hrs. After cooling and removing the product, it was found that 100% of the MAN was converted and that selectivity to NMS was 80% and selectivity to NMP was 15%.

EXAMPLE 3

A 73 g portion of dimethylsuccinate (DMS), 36.6 g of ammonium hydroxide and 12 g of 5% palladium on carbon were sealed in the autoclave which was first purged with argon and then pressured with 900 psig hydrogen. The autoclave was heated to 260° C. and stirred for 16 hrs. After cooling and removal of the product, analysis gave 100% DMS conversion with a 70% NMS selectivity and a 20% NMP selectivity.

EXAMPLE 4

A 65 g portion of SAN, 41 g of methanol, 12.5 g of ammonia, 12 g of reduction catalyst were sealed in the autoclave, the reactor purged with argon, and 700 psig of hydrogen pressured in. The reactor was heated to 290° C. for 21 hours with stirring. The contents of the reactor were cooled, removed and analyzed. A 100 percent SAN conversion was found with a selectivity to NMS of 60% and a selectivity to NMP of 30%.

What is claimed is:

1. A process to form a N-alkylpyrrolidone wherein said alkyl substituent is selected from the group consisting of methyl, ethyl, propyl, isopropyl and butyl substituents comprising:
    converting a compound selected from the group consisting of succinic anhydride, succinic acid, and a dialkyl succinate, where said alkyl is a $C_1$ to $C_4$ alkyl group, to a N-alkylsuccinimide by contacting under reaction conditions said compound with ammonia and the corresponding alcohol selected from the group consisting of methanol, ethanol, propanol, isopropanol and butanol; and
    catalytically reducing said N-alkylsuccinimide with hydrogen to form said N-alkylpyrrolidone.
2. The process of claim 1 wherein said alkyl substituent is methyl, said N-alkylsuccinimide is N-methylsuccinimide, said alcohol is methanol, and said N-alkylpyrrolidone is N-methylpyrrolidone.
3. The process of claim 1 wherein said alkyl substituent is ethyl, said N-alkylsuccinimide is N-ethylsuccinimide, said alcohol is ethanol, and said N-alkylpyrrolidone is N-ethylpyrrolidone.
4. The process of claim 2 wherein said compound is succinic anhydride.
5. A process to form a N-alkylpyrrolidone wherein said alkyl substituent is selected from the group consisting of methyl, ethyl, propyl, isopropyl and butyl substituents comprising:
    catalytically reducing a maleic derivative selected from the group consisting of maleic acid or anhydride with hydrogen to form succinic acid or anhydride;
    converting said succinic acid or anhydride to a N-alkylsuccinimide by contacting under reaction conditions optionally in the presence of a catalyst said succinic anhydride with ammonia and the corresponding alcohol selected from the group consisting of methanol, ethanol, propanol, isopropanol and butanol; and
    catalytically reducing said N-alkylsuccinimide with hydrogen to form said N-alkylpyrrolidone.
6. The process of claim 5 wherein said alkyl substituent is methyl, said N-alkylsuccinimide is N-methylsuccinimide, and alcohol is methanol, and said N-alkylpyrrolidone is N-methylpyrrolidone.
7. The process of claim 5 wherein said alkyl substituent is ethyl, said N-alkylsuccinimide is N-ethylsuccinimide, said alcohol is ethanol, and said N-alkylpyrrolidone is N-ethylpyrrolidone.
8. The process of claim 6 wherein said maleic derivative is maleic anhydride.

* * * * *